United States Patent [19]

Biermaier

[11] Patent Number: 5,795,403
[45] Date of Patent: Aug. 18, 1998

[54] METHOD AND DEVICE FOR CLEANING ENDOSCOPES

[76] Inventor: Hans Biermaier, Ulrichstrasse 47, D-86316 Derching, Germany

[21] Appl. No.: 498,988

[22] Filed: Jul. 6, 1995

[30] Foreign Application Priority Data

Jul. 6, 1994 [DE] Germany ............... 44 23 730.8

[51] Int. Cl.$^6$ ....................................................... B08B 9/02
[52] U.S. Cl. ........................... 134/22.12; 134/22.18; 134/166 C; 134/169 C; 134/57 R; 277/646
[58] Field of Search ................. 134/22.18, 22.12, 134/24, 166 C, 169 C, 198, 170, 113, 56 R, 57 R, 58 R; 137/625.18, 625.27; 138/93; 277/605, 646

[56] References Cited

U.S. PATENT DOCUMENTS

| 1,221,733 | 4/1917 | Henderson . | |
|---|---|---|---|
| 2,182,888 | 12/1939 | Whitaker . | |
| 2,450,308 | 9/1948 | Smith | 134/24 |
| 3,393,744 | 7/1968 | Fagg et al. . | |
| 3,760,878 | 9/1973 | Peevey . | |
| 4,413,655 | 11/1983 | Brown . | |
| 4,484,602 | 11/1984 | Guthrie . | |
| 4,484,626 | 11/1984 | Kerfoot et al. . | |
| 4,537,209 | 8/1985 | Sasa | 134/166 C |
| 4,569,396 | 2/1986 | Brisco . | |
| 4,646,787 | 3/1987 | Rush et al. . | |
| 4,667,691 | 5/1987 | Sasa | 134/169 |
| 4,763,728 | 8/1988 | Lacey . | |
| 5,027,895 | 7/1991 | Barton . | |
| 5,146,939 | 9/1992 | Matthews et al. | 134/198 |
| 5,279,799 | 1/1994 | Moser | 422/292 |
| 5,286,301 | 2/1994 | Albrecht | 134/166 C |
| 5,288,467 | 2/1994 | Biermaier | 422/116 |
| 5,653,819 | 8/1997 | Bee et al. | 134/24 |

FOREIGN PATENT DOCUMENTS

| 0483059A1 | 4/1991 | European Pat. Off. . |
| 341266A1 | 10/1984 | Germany . |
| 3710517A1 | 10/1988 | Germany . |
| 3819257C1 | 7/1989 | Germany . |
| 4025624A1 | 2/1991 | Germany . |
| 4404460C1 | 6/1995 | Germany . |

Primary Examiner—Frankie L. Stinson
Attorney, Agent, or Firm—Senniger, Powers, Leavitt & Roedel

[57] ABSTRACT

For cleaning endoscopes which have at least two channels with one inlet and one outlet that each open into a chamber of the endoscope, wherein the inlets are connectable to a source of cleaning fluid, the invention provides for an insertion element insertable into the chamber of the endoscope head, said insertion element features controllable seals that in the activated state rest against the wall of the chamber and thus form mutually separated annular spaces that communicate with each channel and connect one associated inlet in the sense of the flow with an associated outlet, whereas in the deactivated state they feature a distance between the insertion element and the wall. This ensures that each channel is individually cleaned, and that the cleaning can also be monitored. In order to clean the surface of the chamber covered by the activated seal, the seal is deactivated so that this location can then also be rinsed.

20 Claims, 6 Drawing Sheets

METHOD AND DEVICE FOR CLEANING ENDOSCOPES

BACKGROUND OF THE INVENTION

The invention pertains to a method and device for cleaning endoscopes.

From DE-PS 3,710,517 a washing machine is known for cleaning endoscopes that features a line for cleaning fluids that can be connected to the proximal end of one working channel of the endoscope. By means of this line the working channel is fed directly with cleaning fluid coming from a circulating pump. In addition, this publication describes how an increased pressure difference can be generated for the cleaning fluid flowing along the outer wall of the endoscope. This takes place in that the endoscope tube runs in a hollow tube which is longer than the endoscope tube, so that at the distal end of the endoscope tube, inflow cavitation occurs and thus a vacuum pressure is created that exerts a suction effect on the cleaning fluid flowing through the working channel.

In DE-PS 3,819,257 a similar machine is shown where the endoscope is inserted into a vessel to which cleaning fluid is fed under pressure by a circulating pump of the machine. Provided all channels to be cleaned have roughly the same cross section, the cleaning fluid under pressure then moves from the vessel into these channels.

Finally, from the previous, unpublished German Patent Application P 4,404,460 of the applicant, a cleaning and disinfecting machine is described for endoscopes that feature a pressure booster system fed by the circulating pump in the form of a two-stage piston/cylinder arrangement that is connected to one or more endoscope channels and rinses them at elevated pressure.

Newer endoscopes not only have tighter channels, since increasingly more functions are housed in the endoscope while retaining essentially the same diameter, but they have several mutually separated channels, which have to be cleaned, disinfected and dried. Formerly it was common to supply all these channels jointly from a common source for cleaning and/or disinfecting fluid or for sterilized drying air, for example, by placement of the endoscope head into the vessel according to DE-PS 3,819,257 or through joint connecting of all channels to the pressure booster system of the older patent application P 4,404,460.

Thus all channels to be cleaned are connected in parallel with regard to the flow, with the result being that the greatest portion of the cleaning fluid flows through that particular channel with the largest flow cross section that acts as bypass for the other channels. The tighter channels are thus not cleaned as well, or are even not cleaned at all. If a channel is plugged up entirely, then it will not be cleaned at all if the pressure of the cleaning fluid is not sufficient to eliminate the plugging. Thus there is the danger that the channels of endoscopes will not be cleaned sufficiently, if at all, so that bacteria, germs or other disease agents, and also dirt or even residues of body fluids of other patients may be carried in and then result in infections in subsequent operations.

SUMMARY OF THE INVENTION

The purpose of the invention is to specify a method and a device for cleaning of endoscopes with at least two channels, so that it is assured that all channels are satisfactorily cleaned. This problem is solved by the features described in the claims. Favorable configurations and refinements of the invention are found in the subclaims.

The basic idea underlying the invention is that during the cleaning process, one insertion element is installed in one chamber of the endoscope; this element has controllable seals that separate the individual channels of the endoscope from each other with regard to the flow, so that each channel is cleaned individually.

The seals are thus controllable in order to allow cleaning of the contact surface between seal and the chamber of the endoscope when the seal is opened, since otherwise impurities could settle down there.

At least two controllable seals are provided that are controllable so that during operation at least one seal is forced against the wall of the chamber and thus holds the insertion element securely in place so that it cannot slip off or even accidentally leave the chamber.

The invention provides for different variants. In one variant, a piston is used such that it can be inflated in whole, or in individual sectors; at the outer surface this piston has a annular groove that forms a flow path for water, rinsing fluid or compressed air from an inlet to the chamber of an outlet associated with the channel. The particular inlet and the associated outlet in this case are located at the same height in the chamber but are mutually offset in the circumferential direction.

In another version, only the seals are inflatable by means of a hydraulic medium or compressed air, respectively, whereas in yet another version, a piston equipped with expandable sealing rings or O-rings can be used that pushes the individual sealing elements apart or releases them by means of a stepped, internal piston, so that they can pull together due to their spring action. The internal piston in this case makes a horizontal motion that can be generated by a linear displacement or by a threaded spindle.

In yet another version, an expandable cylinder is inserted automatically into the chamber of the endoscope and expanded so that the unambiguous flow paths are formed from the inlet to the outlet. During the washing process, however, the cylinder is repeatedly withdrawn in order to clean and disinfect the interior walls of the chamber of the endoscope.

According to an additional variant, a mechanical or hydropneumatic device can also be provided that moves the valve located in the chamber of the endoscope and thus creates a pressure-tight connection for the individual inlets and outlets. This valve will also be removed from the chamber one or several times during the washing process in order to clean the inside walls of the chamber.

In all these variants it is thus possible to keep one seal always closed in order thus to ensure a secure mount of the insertion element and thus to prevent release of the insertion element.

Thus this insertion element has two functions, namely to ensure that each channel is rinsed individually, and secondly, to ensure that any existing residual germs on the sealing surface will likewise be removed.

Refinements of the invention provide for the individual operating processes to be monitored and automatically recorded. The monitoring can take place in numerous ways. For example, the pressure profile and/or the quantity of fluid flowing through the individual channels can be detected, either as a function of the time or also as a function of the individual setting of the controllable seals. Thus it can also be dependably verified whether every channel was properly cleaned or whether, for example, one channel is plugged up so that no cleaning fluid can get through it. In this case the invention provides that the channel be rinsed free with increased pressure of the cleaning fluid. And even if this is not successful, at least a warning message will be output.

An additional aspect of the invention rests in the fact that this documentation is maintained individually for each endoscope, wherein the individual endoscope is identifiable by an identifying number or a bar code. In this manner a cleaning machine can document all cleaning actions of an individual endoscope over its entire lifespan. In this case, changes or expansions or contractions of the channels caused by wear can be ascertained, since under otherwise constant parameters, different pressure profiles and/or different fluid quantities flowing per unit time through the individual channels will result.

In addition, an individual cleaning sequence can be specified for each individual endoscope with regard to the various parameters such as cleaning time, pressures, cleaning or disinfecting agents used, etc. For example, in this manner the corresponding, previously saved pressure parameters can be called up automatically for an individual endoscope, as is necessitated due to the different channel diameters. Due to their design, endoscopes always have differing diameter and lengths which then means different back pressures or flow quantities for a validated rinsing. Due to the identification of the individual endoscopes and the preceding tailoring of the required rinsing pressure and rinsing quantities for new or repaired endoscopes, we can also unambiguously determine whether the channels of the endoscope have become tighter, possibly due to dirt or other damage that has hygienic or technical consequences. Due to the documentation feature, a continuous documentation can be maintained in the event that suits for damages are filed against the physician or the clinic due to insufficient hygiene.

One refinement of the invention provides that the endoscope head is inserted into a tightly sealed cassette in the interior of the washing zone, which prevents moisture from getting to certain locations of the endoscope head during the washing process and/or on electronic parts for ultrasonic heads, etc. This cassette is held at high pressure with compressed air during the washing process, in order reliably to prevent the penetration of moisture and condensate. This overpressure is monitored during the washing process by a sensor and is recorded.

Briefly, therefore, the invention is directed to a method for cleaning an endoscope, the endoscope including a head, a chamber in the head, and at least two inlets and two outlets in the head opening through a wall of the chamber into the chamber. The method involves connecting each of the inlets to a source of cleaning fluid, forming seals on the chamber wall to define separate flow paths through the chamber, a first of the flow paths extending from a first of the inlets to a first of the outlets and a second of the flow paths extending from a second of the inlets to a second of the outlets, flushing each flow path with cleaning fluid, and selectively breaking the formed seals to expose portions of the chamber wall for rinsing by the cleaning fluid.

The invention is also directed to a device for cleaning an endoscope, the endoscope including a head having a chamber in the head, and at least two inlets and two outlets in the head opening through a wall of the chamber into the chamber, the inlets being adapted for connection to a source of cleaning fluid. The device has an insertion element insertable into the chamber of the endoscope head, the insertion element having two controllable seals sealingly engaging the chamber wall in an activated state of the controllable seals to form mutually separated annular spaces that respectively connect a first of the inlets with a first of the outlets and a second of the inlets with a second of the outlets. The controllable seals each have a deactivated state in which the controllable seal is not sealingly engaged with the wall of the chamber.

Other objects and features of the invention will be in part apparent and in part pointed out hereinafter.

BRIEF DESCRIPTION OF THE DRAWINGS

The invention will be explained in greater detail below based on several design examples in connection with the figures.

The same reference numbers in the individual figures denote the same or functionally corresponding parts.

DETAILED DESCRIPTION OF THE INVENTION

Figure 1:
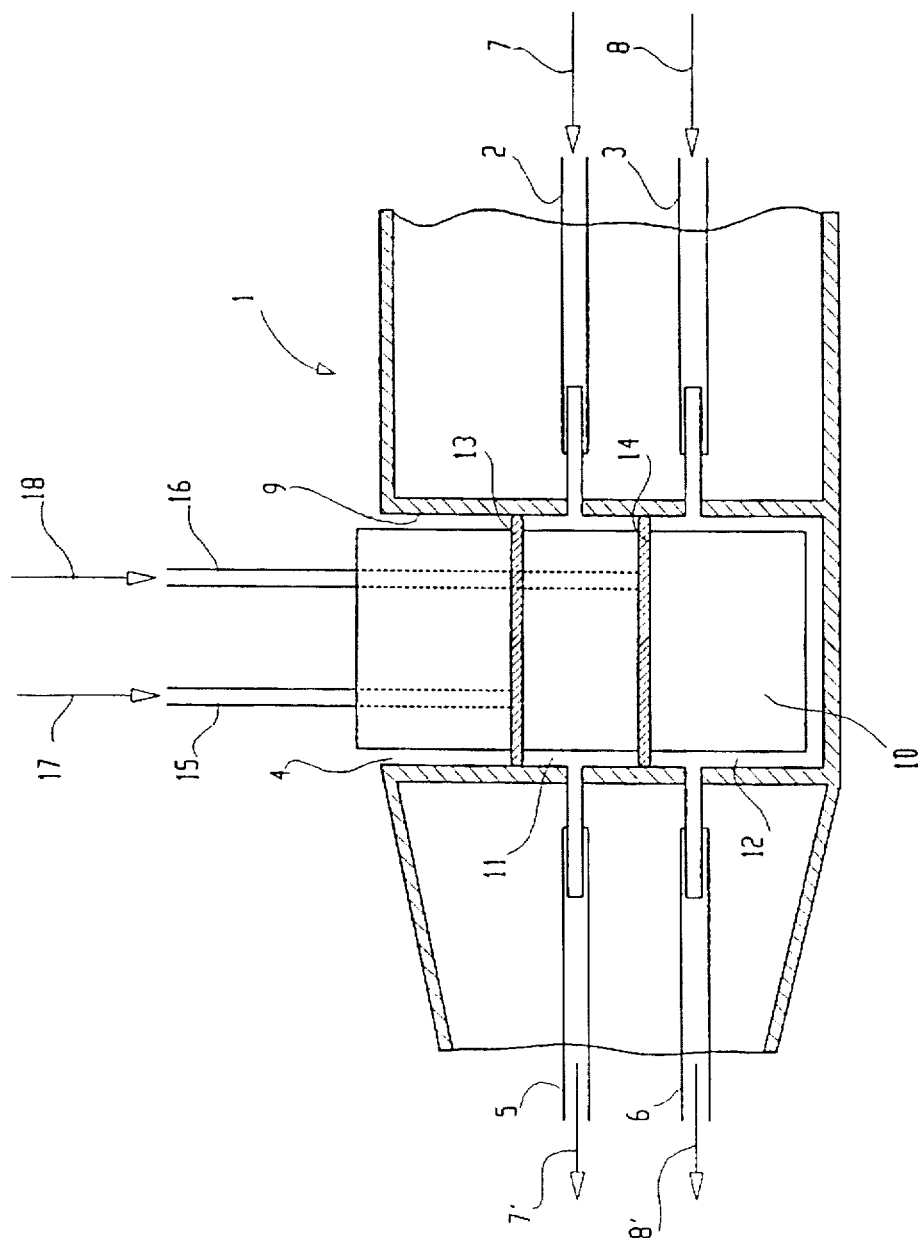
FIG. 1: A schematic cross section through a device according to the invention, which is inserted into an endoscope head, according to a first embodiment example of the invention.

FIG. 1 shows schematically a section of an endoscope head 1 wherein in this representation only the channels to be cleaned are shown and all other parts of the endoscope and/or the entire optical system and any existing electronic units etc., have been omitted. The endoscope head 1 features a first connection 2 and a second connection 3 to which in the normal use of the endoscope, water for example, and/or compressed air is fed. These two connections 2 and 3 open into a cylindrical chamber 4 which contains valves in normal use of the endoscope. In addition, this chamber 4 has a number of inlets corresponding to the number of outlets, i.e., in the illustrated embodiment example, a first outlet 5 assigned to the first inlet 2 and a second outlet 6 assigned to the second inlet 3, which is indicated by the arrows 7, 7' and 8, 8', which denote the direction of flow.

For cleaning the channels of the endoscope, the inlets 2 and 3 are each separately connected to a source for cleaning and/or disinfecting fluid, wherein this fluid flows along the arrow 7 into the inlet 2 and along the arrow 7' from the outlet 5 and thus flows into the channel of the endoscope being cleaned. Accordingly, the fluid flows in the direction of the arrow 8 from the inlet 3 to the outlet 6 and in the direction of the arrow 8' through the associated channel.

In order to achieve these flow directions and a separation of the flow paths, an insertion element 10 is installed in the chamber 4 for the cleaning process, said element forming two separate annular spaces 11 and 12 between its mantle surface and the inner wall 9 of the chamber 4. The first annular space 11 thus forms one flow path from the inlet 2 to the outlet 5, whereas the second annular space 12 forms a flow path from the second inlet 3 to the second outlet 6. These two annular spaces are delimited by means of controllable seals 13 and 14 in the axial direction of the insertion element. These controllable seals 13 and 14 can be controlled so that they take on either a working position in which they rest against the inside wall 9 of the chamber 4, or an "at rest" position in which they are located at a distance to the inside wall 9 of the chamber 4, so that then in this rest position, the contact surface between the seal and the inner wall 9 is exposed and is accessible to the cleaning fluid. The first controllable seal 13 is located above the first inlet 2 and the first outlet 5—viewed from the opening side of the chamber 4—whereas the second controllable seal 14—viewed from the inlet side of the chamber 4—is located underneath the first inlet 2 and the first outlet 5, but above the second inlet 3 and the second outlet 6. In other words, the second seal 14 is located between the first flow path from the inlet 2 to the outlet 5 and the second flow path from the inlet 3 to the outlet 6.

In the embodiment example according to FIG. 1, the controllable seals 13 and 14 are controllable by means of compressed air which is fed via connector 15 or 16 to these inflatable seals, which is indicated by the arrows 17 and 18.

In the position shown in FIG. 1, compressed air strikes both controllable seals 13 and 14 so that they are in their working positions, where they rest against the inside wall 9 of the chamber 4, thus forming a seal of the annular space 11 toward the outside of the endoscope and toward the second annular space 12. Due to the controllable seal 14, the annular space 12 is also simultaneously sealed with respect to the annular space 11. It is evident that in this setting, the two flow paths lead from the first inlet 2 across the annular space 11 to the outlet 5 on the one hand, and from the second inlet 3 across the annular space 12 to the second outlet 6 on the other, and are completely separated from each other wherein the fluids are carried along a forced path.

Since the contact surfaces between the seals 13 and 14 on the one hand and the inner wall 9 of the chamber 4 on the other can be soiled and thus require cleaning, the two seals 13 and 14 are separately controllable, and according to one version of the invention, they are operated so that at a particular time within a cleaning cycle, one seal is in the working position and the other is in the rest position. For example, if the first seal 13 is in the working position and the second seal 14 is in the rest position, then cleaning fluid flows from both inlets 2 and 3 into the annular spaces 11 and 12, which are connected together with regard to the flow, and thus also cleans the contact site between the second seal 14 and the inner wall 9. Then the first seal 13, now in its working position, holds the insertion element 10 in its position within the chamber 4.

For cleaning the point of contact between the first seal 13 and the inside wall 9, the second seal 14 is brought into its working position, whereas the first seal 13 goes into the rest position, so that in this position, the fluid flows from the inlet 2 into the first annular space 11, and from there to the point of contact between the first seal 13 and the inside wall 9.

For insertion and removal of the insertion element 10, the two controllable seals 13 and 14 are brought into their deactivated position at rest. The activation and deactivation of the controllable seals 13 and 14 are performed by a program control, which will be discussed in greater detail below, in connection with FIG. 6.

Figure 2:
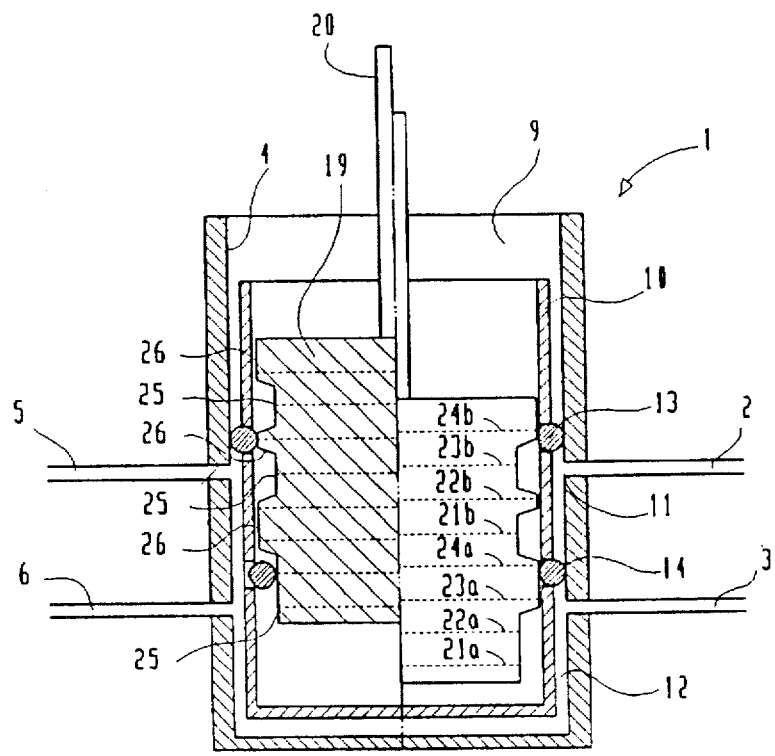
FIG. 2: An illustration similar to FIG. 1 of a second embodiment example of the invention.

FIG. 2 shows another version of the invention, where the controllable seals 13 and 14 are controlled not by a presurized medium, but by the displacement of an inner piston 19.

The insertion element 10 features two annular grooves in which resilient seals, for example, in the form of rubber O-rings 13 and 14, are used. There is a displaceable, inner piston 19 inside the insertion element 10 that can be moved by means of a piston rod 20. This piston features recesses 25 and protrusions 26 mutually offset in the axial direction which define the different switch settings 21a–24a and 21b–24b for the individual seals. In the position of the inner piston 19 shown in FIG. 2, the switch settings 24a and 24b are activated, in which both seals 13 and 14 are pressed outward by protrusions 26 against the inner wall 9 of the chamber. In the position shown on the left side of FIG. 2, however, the first seal 13 is activated, that is, it is pressed outward by the protrusion 26, whereas the second seal 14 is deactivated, that is, it rests in the recess 25 of the inner piston 19 due to the spring force of the O-ring. All possible variants can be implemented with the four switch settings 21 to 24. The inner piston 19 can be displaced by any kind of known feature into the individual switch settings, for example, due to a hydraulic or pneumatic piston, a stepper motor, a linear motor, a magnetic coil, a crank-type drive, etc. The transitions between the recesses 25 and the protrusions 26 are beveled to allow the seals 13 and 14 to slide on or off during a linear displacement of the inner piston 19.

Figure 2A:
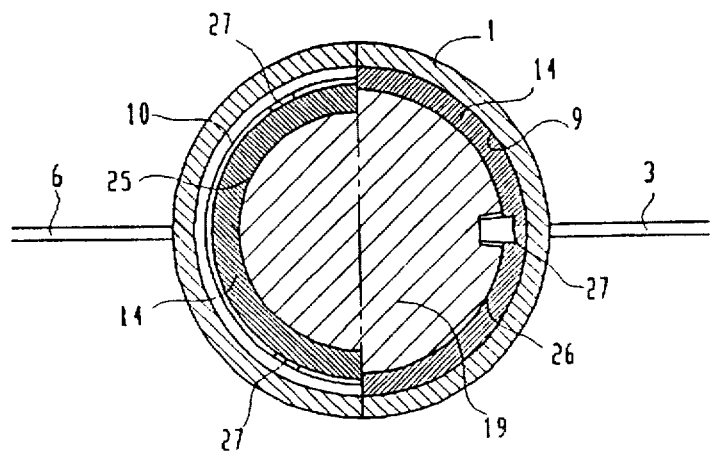
FIG. 2a: A cross section of the device, wherein the cut line runs through the lower seal 14.

As indicated in FIG. 2a, the protrusions 26 are designed as segments that feature recesses into which bars 27 engage that bridge the annular grooves of the insertion element 10 which holds the seals 13 and 14, and thus hold the insertion element 10 together. This will also ensure that when removing the inner piston 19, the sealing rings 13 and 14 do not move completely into the interior of the insertion element, but rather are held against the bars 27.

Figure 3:
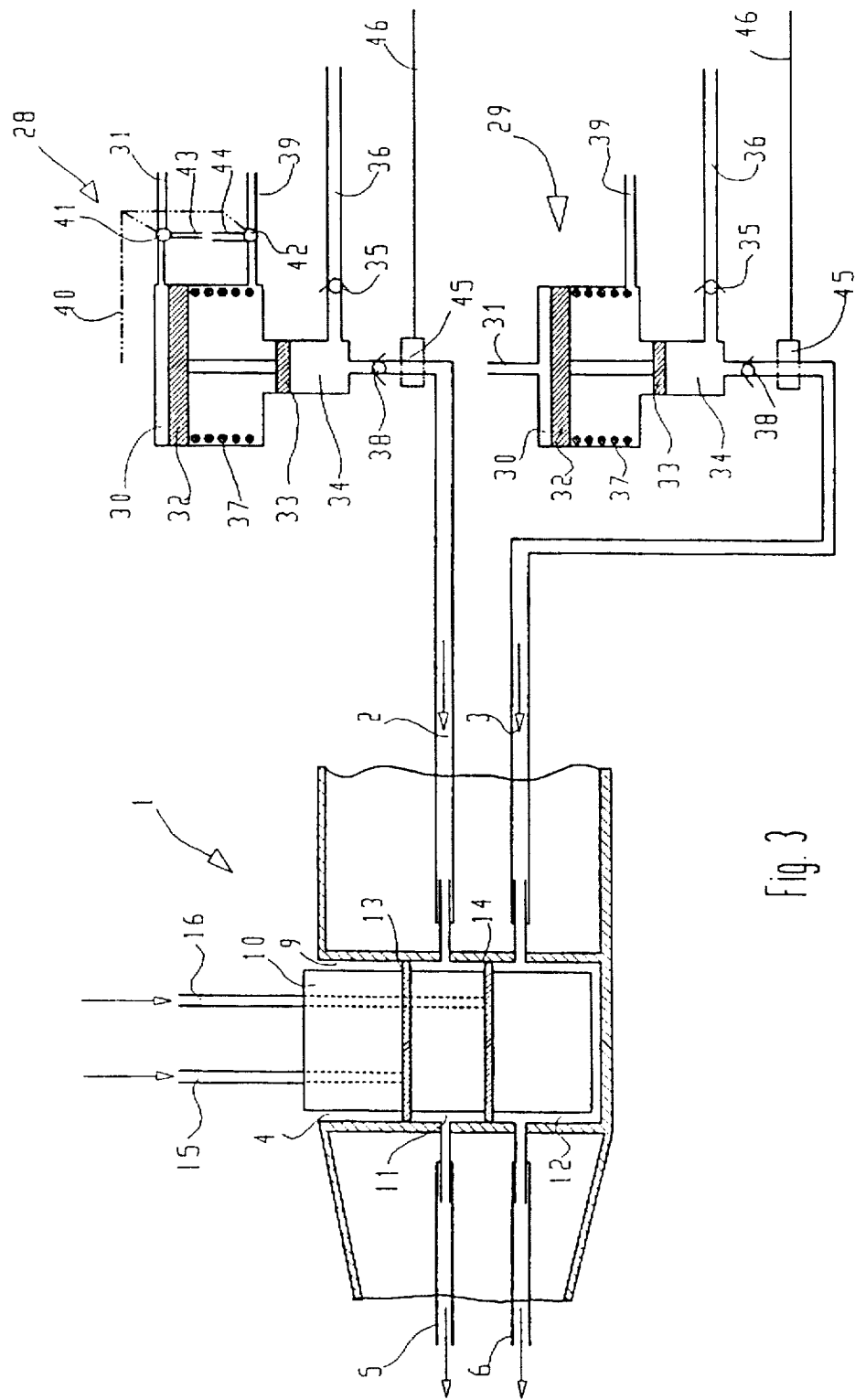
FIG. 3: An illustration similar to FIG. 1 with pressure booster device connected to the individual channels being cleaned.

The embodiment example according to FIG. 3 is identical to that shown in FIG. 1 with regard to the endoscope head 1 and the insertion element 10, but it shows how the two inlets 2 and 3 are separately connected to suitable sources for pressurized rinse fluid. A first pressure elevation unit 28 is connected to the inlet 2 and a second pressure elevation unit 29 is connected to the inlet 3, wherein two variants of pressure elevation units are shown here. In both cases we are dealing with a two-stage piston-cylinder arrangement that is housed in the washing zone of the machine. The two-stage cylinder features a first chamber 30 that is struck by a pressurized rinsing fluid via an opening 31 which presses against a first, large cross-sectional stage of a piston 32. A second stage 33 of the piston with smaller cross section is located in a second chamber 34 which can draw cleaning fluid from the wash zone of the machine via a nonreturn valve 35 and an opening 36 to the second chamber 34 when the two pistons 32 and 33, which are connected together, move into a rest position due to the force of a spring 37. In this rest position, the second chamber 34 is assumed to be entirely filled with cleaning fluid. As soon as the circulating pump of the machine is switched on and thus pressurized cleaning fluid moves to the wash zone, the first chamber 30 is struck by a rinsing agent standing under pressure via the opening 31, so that the two pistons 32 and 33 are pressed against the force of the spring 37 and thus empty the second chamber 34. The second chamber 34 is connected via a nonreturn valve 38 to an associated inlet 2 or 3 of the endoscope, so that cleaning fluid is forced into these inlets under elevated pressure.

If the circulating pump of the machine is switched off, then the pressure in the first chamber 30 drops and the pistons 32 and 33 move back into their starting position due to the spring force. During this process, the nonreturn valves 38 are closed and the nonreturn valves 35 are opened, so that the second chambers 34 are again filled with new cleaning fluid by means of the openings 36. To this extent the two pressure elevation units 28 and 29 coincide. But there are differences with regard to the control. The second pressure elevation unit 29 is controlled only by means of the pressure of the circulating pump, wherein the gap between the two pistons 32 and 33, which also holds the spring, is connectable via a drain opening 39 to outside air.

In the first pressure elevation unit, switching valves are installed in the feed lines to the openings 31 and 39; these valves are actuated via a linkage 40 that is coupled to the piston 32. In the rest position, in which the pistons are brought into their limiting position by the spring 37, one switching valve 41 is in the position so that the chamber 30 is connected to the opening 31, whereas the gap between the two pistons 32 and 33 is at atmospheric pressure, that is, it is connected to the opening 39. If the piston 32 moves into a lower limiting position, then the two switching valves 41 and 42 will switch so that the first chamber 30 is connected via an opening 43 to the outside pressure, whereas the gap between the two pistons 32 and 33 is connected to an opening 44 that is located in the interior of the machine and is subjected to the pressure of the delivery pump of the machine. Thus the space between the two pistons 32 and 33 is subjected to pressure, and the two pistons 32 and 33 are pressed upward due to this pressure and due to the force of the spring 37, so that ultimately the up and down movement of the two pistons 32 and 33 is produced, and in spite of continuously operating the delivery pump on the machine, a multiple pressure cleaning of the connected channel occurs.

Instead of this type of pressure elevation unit, of course any other type of pressure elevation units could be used, for example, delivery pumps controllable to a particular pressure or proportional valves fed from a source of hydraulic medium or other known devices.

In the feed line between the pressure elevation unit and the inlets 2 or 3, an additional measuring element 45 is installed that can be, for example, a pressure measuring device or a flowmeter, which determines the quantity of fluid that has flowed through. By means of an electric line 46 connected with the machine controller (not illustrated) a signal is output to the controller which corresponds to the current pressure. By means of the temporal profile of this pressure we can determine the cross section of the channel to be cleaned, or whether any cleaning fluid has flowed through the channel, since the pressure in the second chamber 34 must drop when the piston moves into the lowest position.

If the measuring element 45 is a flowmeter, then the quantity of the cleaning fluid sent through the particular channel can be determined. Given a known volume of the second chamber 34 the pressure and/or the cross section of the channel being cleaned can be determined by means of the temporal profile. But it is also possible to use the combined pressure and flowmeter to measure the desired parameters.

At this point let us stress that the described pressure elevation unit in all embodiment examples of FIGS. 1 to 6 can be used.

Figure 4:
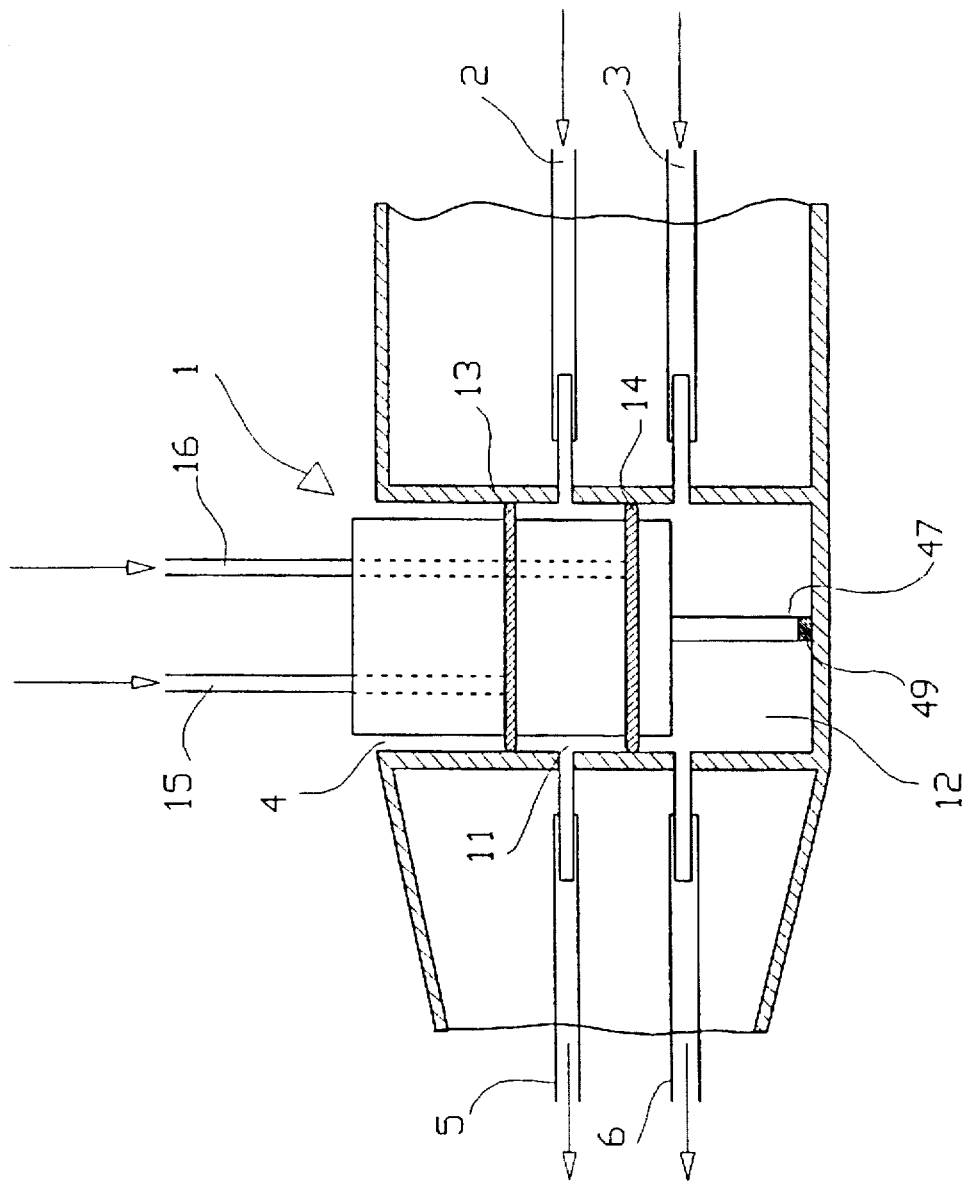
FIG. 4: A view similar to FIG. 1 for a fourth embodiment example of the invention.

Compared to FIG. 1, in FIG. 4 we see a slightly modified version where the insertion element 10 is shorter and does not extend down to the base of the chamber 4. But for precise positioning, it is possible, for example, for the insertion element 10 to have a protrusion 47 that ensures an axial positioning of the insertion element. So that the contact point between this protrusion 47 and the base of the chamber 4 can also be cleaned, it is possible to design this protrusion 47 as displaceable, for example, so that it is displaceable as a whole with a small piston-cylinder arrangement that is actuated by an additional control line or by the control line 16. The latter is particularly useful so that the entire annular space can be cleaned when releasing the controllable seal 14 and thus also withdrawing of the protrusion 47. Instead of a piston/cylinder arrangement for displacement of the protrusion 47, one could also provide at the lower end of the protrusion 47, an inflatable balloon 49 that is activated together with the second controllable seal 14. With the initial insertion of the insertion element 10 into the chamber 4, this balloon 49 is not yet inflated. Rather, the insertion element is inserted up to the stop of the protrusion 47 against the base of the chamber 4. As soon as pressure is applied to the control line 16, the balloon 49 inflates, pushing the insertion element 10 back somewhat, so that it is correctly positioned.

Figure 5:
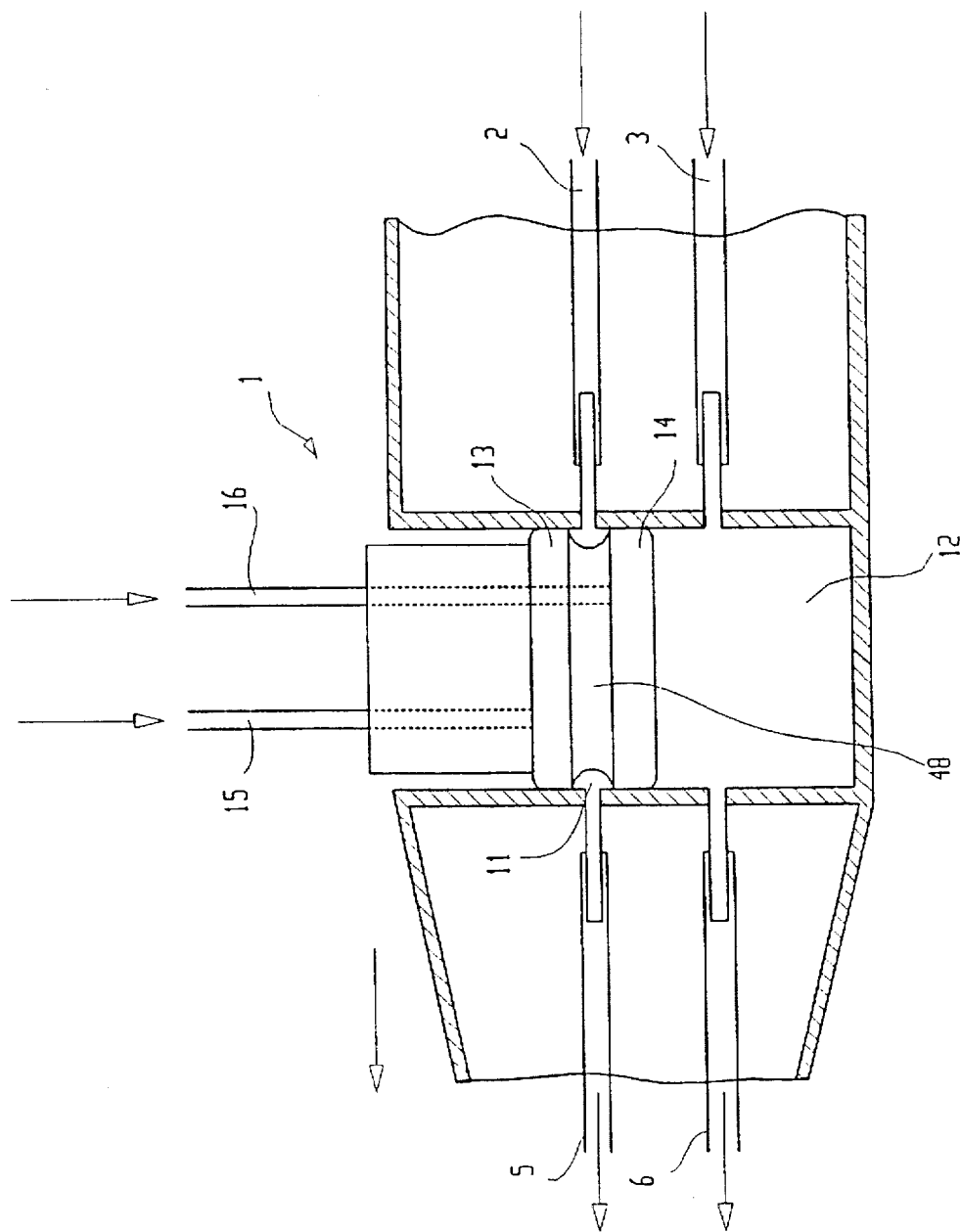
FIG. 5: A view similar to FIG. 1 for a fifth embodiment example of the invention.

FIG. 5 shows another version of the invention where the insertion element features two separately inflatable chambers that form the controllable seals 13 and 14. Each of these chambers is connected to one of the control lines 15 or 16, respectively. The region between these chambers is equipped with a ring 48 of rigid material that has a smaller radius than the two seals 13 and 14 in the inflated state, so that the annular space 11 is formed. Underneath the second controllable seal 14 there is now the annular space 12. Axial positioning can take place in the same way as in the embodiment example of FIG. 4. Operation, together with activation and deactivation of the individual controllable valves, is otherwise the same as was described in detail in the embodiment example of FIG. 1.

In this version, it is also possible for the two controllable seals 13 and 14 to be only inflated and deflated jointly. In this case, it must be ensured either that the insertion element remains in position with the deflated seals or that it is pulled out and repositioned later.

Figure 6:
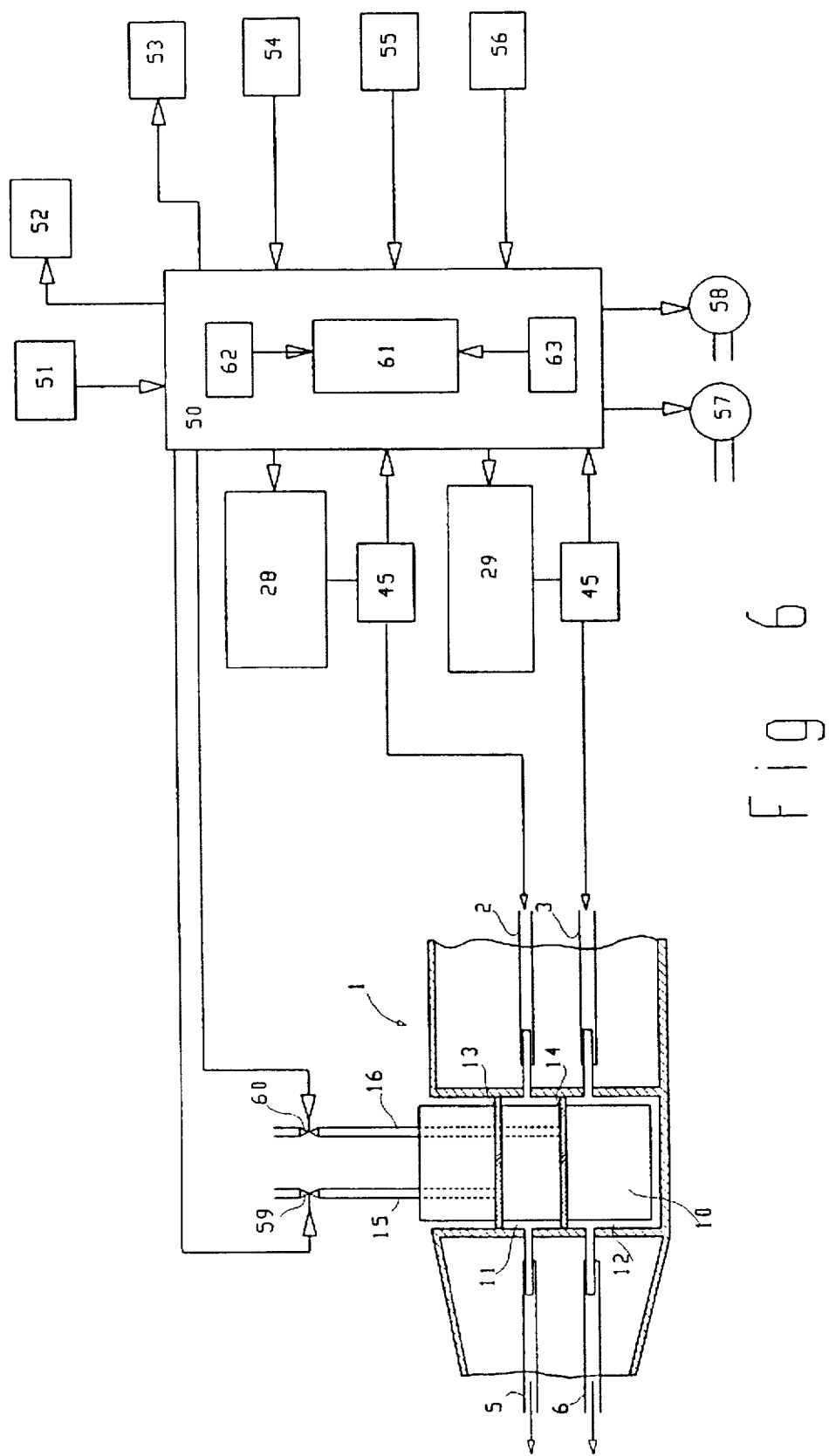
FIG. 6: A basic flow chart of the controller in conjunction with the device according to the invention.

FIG. 6 shows a schematic flow chart of the machine controller. The two inlets 2 and 3 are each connected—as described in conjunction with FIG. 3—to a pressure elevation unit 28 or 29, wherein in this connecting line there is one measuring organ 45 or 45' that outputs an electrical measuring signal to a controller 50. An identification device 51 is also connected to the controller; said identification device can be a bar code reader, for instance, and transmits data which identifies an individual endoscope to the controller 50. In addition, a display device 52 or a screen, an additional output device 53 or a printer, an external memory or similar device are connected to the controller, and also an input device 54 which can be a keyboard, for instance, and also various sensors 55 and 56 which in this case are provided as examples to stand for a number of possible measuring sensors. For example, the measuring sensors can contain one or several temperature sensors, a door contact, a pressure sensor to check for leaks, a sensor for excessive foam formation, etc.

The controller 50 in the present embodiment example controls two pumps 57 and 58 and also the two pressure elevation units 28 and 29, and finally also the two controllable seals 13 and 14, and specifically by means of solenoids 59 and 60 through which a hydraulic medium or compressed air is fed to the two seals or through which these seals are vented. Preferably 3-way valves are used as solenoids here; they have three settings: increase pressure, hold pressure and release pressure.

The controller 50 contains a microprocessor 61, a program memory 62 and a data memory 63, and also the standard assemblies (not illustrated) such as power supply, interface circuits, etc., wherein the input and output devices are in communication with the microprocessor 61.

If an endoscope is to be cleaned, then before it is inserted into the machine it is identified by the bar code reader 51, so that the microprocessor 61 then calls up from the data memory the parameters for this endoscope previously programmed and stored therein. In addition, the insertion element 10 is installed into the chamber of the endoscope and all connections (for inlets 2 and 3, control lines 15 and 16 and electrical connectors of the solenoids 50 and 60) are established. The operator then selects via the keyboard 54 the desired cleaning program since it will then be displayed on the monitor together with all important parameters or can be output on the printer 53. Depending on the selected program and on the parameters characteristic for the individual endoscope, the cleaning program then proceeds and in accordance with a previously saved program, the controller activates the individual assemblies and/or the pumps 57 and 58, the pressure elevation units 28 and 29, the solenoids 59 and 60 etc., and simultaneously documents all essential data which can be saved in the data memory 62 and optionally displayed on the monitor 52 or output on the printer 53.

One refinement of the invention provides that the endoscope head is inserted into a tightly sealed cassette 70 in the interior of the washing zone, which prevents moisture from getting to certain locations of the endoscope head during the washing process and/or on electronic parts for ultrasonic heads, etc. This cassette is held at high pressure with compressed air during the washing process, in order reliably to prevent the penetration of moisture and condensate. This overpressure is monitored during the washing process by a sensor 71 and is recorded. A fluid-tight container of this type is shown in U.S. Pat. No. 5,288,467, the entire disclosure of which is expressly incorporated herein by reference.

In view of the above, it will be seen that the several objects of the invention are achieved and other advantageous results attained.

As various changes could be made in the above construction and methods without departing from the scope of the invention, it is intended that all matter contained in the above description or shown in the accompanying drawings shall be interpreted as illustrative and not in a limiting sense.

What is claimed is:

1. A method for cleaning an endoscope, the endoscope including a head, a chamber in the head, and at least two inlets and two outlets in the head opening through a wall of the chamber into the chamber, the method comprising the steps of:

connecting each of said inlets to a source of cleaning fluid;

forming seals on the chamber wall to define separate flow paths through the chamber, a first of the flow paths extending from a first of the inlets to a first of the outlets and a second of the flow paths extending from a second of the inlets to a second of the outlets;

flushing each flow path with cleaning fluid; and selectively breaking the formed seals to expose portions of the chamber wall for rinsing by the cleaning fluid.

2. A device for cleaning an endoscope, the endoscope including a head having a chamber in the head, and at least two inlets and two outlets in the head opening through a wall of the chamber into the chamber, the inlets being adapted for connection to a source of cleaning fluid, the device comprising an insertion element insertable into the chamber of the endoscope head, said insertion element having two controllable seals sealingly engaging the chamber wall in an activated state of the controllable seals to form mutually separated annular spaces that respectively connect a first of the inlets with a first of the outlets and a second of the inlets with a second of the outlets, the controllable seals each having a deactivated state in which the controllable seal is not sealingly engaged with the wall of the chamber.

3. The device according to claim 2 wherein said controllable seals are separately controllable between activated and deactivated states.

4. The device according to claim 3 wherein the controllable seals are expandable by a medium under pressure.

5. The device according to claim 4 wherein the medium under pressure is compressed fluid.

6. The device according to claim 3 wherein said controllable seals comprise resilient rings and wherein the insertion element further comprises annular grooves into which the resilient rings are installed and an axially displaceable inner piston in the insertion element's interior, the inner piston having protrusions and recesses offset in the axial direction.

7. The device according to claim 2 wherein said controllable seals comprise resilient rings and wherein the insertion element further comprises annular grooves into which the resilient rings are installed and an axially displaceable inner piston in the insertion element's interior, the inner piston having protrusions and recesses offset in the axial direction.

8. The device according to claim 7 wherein the controllable seals are jointly controllable, the device further comprising a ring between the controllable seals that has a smaller diameter than the seals in their expanded state to form an annular space between the seals.

9. The device according to claim 2 wherein the controllable seals are jointly controllable, the device further comprising a ring between the controllable seals that has a smaller diameter than the seals in their expanded state to form an annular space between the seals.

10. The device according to claim 9 wherein the insertion element is constructed for insertion into the chamber or withdrawal from the chamber during a cleaning process.

11. The device according to claim 2 wherein the insertion element comprises a protrusion for axially positioning the insertion element in the chamber.

12. The device according to claim 11 wherein the protrusion is controllable such that it can be extended and retracted.

13. The device according to claim 12 wherein the protrusion is controllable by a balloon which is expandable by a medium under pressure.

14. The device according to one of claims 2 wherein each inlet is connectable to a separate pressure booster unit that feeds the cleaning fluid at elevated pressure to the associated flow path.

15. The device according to claim 2 comprising a separate measuring element for each flow path that measures a value selected from the group consisting of a pressure value, a cleaning fluid quantity flow value, and both a pressure value and a cleaning fluid quantity flow value, each of said separate measuring elements sending to a controller a signal that corresponds to the measured value.

16. The device according to claim 15 wherein the controller saves values measured by the measuring element at specified time intervals.

17. The device according to claim 16 wherein a reader is connected to the controller, said reader being capable of reading a marking supplied on each endoscope which marking identifies the endoscope, the controller being capable of recalling previously saved measured values for the cleaning process for the identified endoscope. comparing presently measured values to previously saved measured values during the cleaning process and putting out a message in the event of differences between presently measured values and previously saved measured values.

18. The device according to claim 16 wherein the controller comprises a data memory that saves all measured values during the cleaning process and optionally documents them on an output device.

19. The device according claim 2 in combination with the endoscope, and wherein the endoscope head is insertable into a fluid-tight cassette whose interior is connectable to a compressed air source.

20. The device in combination with the endoscope according to claim 19 wherein a pressure gauge is provided that monitors the pressure in the interior of the cassette.

* * * * *